United States Patent [19]

Stuart et al.

[11] Patent Number: 4,865,980
[45] Date of Patent: * Sep. 12, 1989

[54] MONOCLONAL ANTIBODIES FOR DNA-RNA HYBRID COMPLEXES AND THEIR USES

[75] Inventors: W. Dorsey Stuart, Honolulu, Hi.; Mark B. Frank, Irvine, Calif.

[73] Assignee: University of Hawaii, Honolulu, Hi.

[*] Notice: The portion of the term of this patent subsequent to Mar. 22, 2005 has been disclaimed.

[21] Appl. No.: 155,359

[22] Filed: Feb. 12, 1988

Related U.S. Application Data

[63] Continuation of Ser. No. 454,317, Dec. 29, 1982, Pat. No. 4,732,847, which is a continuation of Ser. No. 271,769, Jun. 9, 1981, abandoned.

[51] Int. Cl.$^4$ .................... C12Q 1/68; G01N 33/577; A61K 39/395
[52] U.S. Cl. .................... 435/240.27; 435/6; 435/7; 435/172.2; 530/387; 424/85.8; 935/104
[58] Field of Search ............... 435/6, 7, 172.2, 240.27; 530/387; 424/85.8; 935/104

[56] References Cited

U.S. PATENT DOCUMENTS 4,732,847  3/1988  Stuart et al. ............................ 435/6

Primary Examiner—Margaret Moskowitz
Assistant Examiner—Abdel A. Mohamed
Attorney, Agent, or Firm—Richard L. Neeley

[57] ABSTRACT

Monoclonal antibodies are provided capable of distinguishing DNA-RNA hybrid complexes from single stranded DNA and RNA and double stranded DNA and RNA. The antibodies find particular use in determining the presence of a specific nucleic acid sequence on a solid surface. Single stranded polynucleotide is fixed to a solid (gel) surface and then hybridized with the complementary probe. The hybrid complex specific monoclonal antibody is then added to bind to any hybrid complexes which have formed. By appropriate label, the hybrid complex may be visualized in a variety of ways.

3 Claims, No Drawings

MONOCLONAL ANTIBODIES FOR DNA-RNA HYBRID COMPLEXES AND THEIR USES

This is a continuation of Ser. No. 454,317, filed Dec. 29, 1982, now U.S. Pat. No. 4,732,847, which is a continuation of application Ser. No. 271,769 filed June 9, 1981, now abandoned.

BACKGROUND OF THE INVENTION

1. Field of the Invention

The discovery of monoclonal antibodies created the opportunity to prepare compositions which could bind to a specific polar and spatial organization, referred to as an epitopic site or determinant site. Polyclonal antibodies had previously found a broad spectrum of applications, particularly in the diagnostic area. The heterogeneity of the polyclonal antisera was conceived to provide advantages and disadvantages to the specificity of the antisera. The polyclonal antibodies provided an average response to a particular structure, which could have the cumulative effect of high specificity, high binding constant and high titer. However, monoclonal antibodies could provide a number of unique opportunities with antigenic compositions which have a plurality of determinant sites. By being able to select for a specific determinant site, rather than having a mixture of antibodies capable of recognizing a plurality of determinant sites, new approaches to the detection of a variety of antigens became possible.

For the most part, the use of monoclonal antibodies has been directed to the detection of antigens, macromolecular proteins having a plurality of determinant sites. The potential for using monoclonal antibodies in other situations has not received attention.

2. Description of the Prior Art

Stuart and Porter (1978) Exp. Cell Res. 113, 219-222 describe the production of antibodies to RNA-DNA hybrid duplexes for forming in situ hybrids on polytene chromosomes as an antigenic test system. Frank et al. (1980) Genetics 94, s33-s34 (abstr.) reported the preparation of monoclonal antibodies in progress. Rudkin and Stollar (1977) Nature (London) 265, 472-473 describe polyclonal antibody binding to polytene chromosomes. Stollar (1970) Science 169, 609-611 describes the preparation of rabbit antibodies to poly(rA).poly(dT) hybrids.

SUMMARY OF THE INVENTION

Monoclonal antibodies highly specific for hybrid DNA-RNA duplexes are provided. The monoclonal antibodies may be labeled directly or indirectly to provide means for detecting DNA or RNA, which may be a fragment or a portion of a much larger polynucleotide, such as a chromosome. By in situ denaturation and hybridization of double stranded DNA, the single strands may be affixed to a solid support, then complexed with RNA and detected using labeled monoclonal antibody, labeled either directly or indirectly, with a label which provides a detectable signal.

DESCRIPTION OF THE SPECIFIC EMBODIMENTS

The subject invention is concerned with the preparation and use of monoclonal antibodies specific for hybrid DNA-RNA duplexes in detecting the presence of a specific sequence employing in situ hybridization. The subject method can be used for the determination of a particular DNA or RNA sequence using a variety of techniques and labels. The subject method can find application in hybrid DNA technology, disease diagnosis, gene identification, DNA and RNA isolation, etc.

The monoclonal immunoglobulins may be any of the conventional immunoglobulins or fragments thereof. Included among the immunoglobulins are IgA, IgD, IgE, IgG and IgM. For the most part, the immunoglobulins of interest will be IgG and IgM. In some instances, it may be desirable to use fragments of immunoglobulins, particularly Fab and F(ab')$_2$ or other convenient fragment which maintains the desired specificity.

The monoclonal antibodies can be prepared by the method of Oi and Herzenberg (1980) in Selected Methods in Cellular Immunology, eds. Mishell and Shiigi (Freeman, San Francisco) pp. 351-372. While any vertebrate may be used, for the most part mice find use. Conveniently, the mouse is immunized against the duplex by having DNA-RNA hybrid duplexes bound to an antigen and the antigen injected into the mice in accordance with conventional ways. After a sufficient time, the spleen is removed from the mouse and the splenocytes crossed with an appropriate myeloma fusion partner to produce hybridomas. The hybridomas may then be used for injection into the peritoneal cavity of a mouse for production of ascites fluid, which may be extracted and used as an enriched source of the desired monoclonal antibodies.

The subject method may be used for the detection of specific sequences of nucleic acids from a wide variety of sources. Normally, a unique sequence will require at least 12 nucleotides, more usually about 18 nucleotides and the complementary strand or probe may be of any size. As a matter of convenience, usually the complementary strand or probe will be less than about 10,000 nucleotides, more usually less than about 5,000 nucleotides, but this is primarily a matter of convenience and not critical to the operability of the subject invention. The source of the DNA may be single stranded or double stranded DNA. The DNA may be chromosomal DNA, including nuclear, mitochondrial, plastid e.g. chloroplast, viral, phage, or the like. Alternatively, the DNA may be from an extrachromosomal source, such as plasmids, double minutes, transposons, ars containing fragments, or the like.

In addition to elements which may be stably maintained in a host cell, DNA fragments of varying size may also be detected. The fragments may be naturally occurring or synthetic, may involve wild type, allelic or mutant genes, including structural genes, regulatory genes, multimers, inverted repeat features, or the like.

RNA can come from various sources, both natural or synthetic. Various types of RNA include messenger RNA, ribosomal RNA, nucleolar RNA, transfer RNA, viral RNA, and heterogeneous nuclear RNA, or the like. In addition, whole naturally occurring entities or fragments thereof may be involved.

To form the hybrid complex, DNA or RNA sequences complementary to the sequence of interest will be employed. These can be derived from naturally occurring sequences, employing the entire sequence or fragment thereof. Single strands will be employed which will normally be of at least 12 nucleotides, more usually of at least about 18 nucleotides, and can be of 30 nucleotides or greater. Particularly, where the nucleotide sequence is obtained from a naturally occurring source, large sequences can be obtained as naturally occurring e.g. messenger RNA, as fragments by mechanical shearing or restriction enzyme cleavage of nucleic acids, such as chromosomes, or the like. Single strands can be isolated by denaturation of double stranded DNA under elevated temperature conditions in an aqueous medium, normally having such additives as formamide, salts, or the like to enhance the rate of melting of the DNA and maintain its single stranded character.

In many cases it will be convenient and desirable to use messenger RNA as a probe. The messenger RNA may be used in-tact or may be cleaved to provide smaller fragments. Messenger RNA may be isolated from other RNA by passage through an oligo-dT column. Where the sequence of interest is a major expression product, the messenger RNA is particularly useful. However, where the DNA has introns, the use of messenger RNA may not prove useful. In many situations, therefore, synthetic sequences may be prepared or once a sequence is determined, it may be readily cloned and used repetitively.

The probe may be a single composition or a mixture of compositions which may be segregated by molecular weight range, migratory aptitude in an electric field, density, or combinations thereof. Various techniques can be used for the purification of sequences or probes, such as electrophoresis, sucrose or cesium chloride gradient fractionation, treatment with a specific binding column, such as oligo-dT for messenger RNA, combinations thereof, or the like.

The single stranded polynucleotide will be fixed to a solid support, either covalently or non-covalently. By fixed is intended that under the conditions of the hybridization and assay, there will be no significant migration of the polynucleotide. By solid support is intended both solid and semi-solid supports. Supports can include glass slides, container walls, membranes, paper, gels, and the like. The solid supports may be coated or functionalized to provide better adherence of the single stranded polynucleotide to the support.

Various techniques may be employed for preparation of the sample for in situ hybridization. In one technique, particularly with chromosomes or other large polynucleotides, the DNA is fixed with a mildly acidic aqueous solution e.g. from about 25 to 75% of a carboxylic acid and then frozen. Post fixing involves employing a mildly acidic alkanolic solution e.g. ethanol-acetic acid, followed by storage in an alkanol, e.g. ethanol. The usual treatment involves an alkanolic-carboxylic acid mixture which may vary from about 1:3–3:1, followed by freezing and then storage in an alkanol e.g. 95% ethanol.

Alternatively, colony hybridization may be employed as described in the now classical paper by Grunstein and Hogness, Proc. Nt. Acad. Sci. U.S.A. 72, 3961–3965 (1975). Colonies are formed on filters with replica plating on an agar plate. Solutions are applied to the underside of the filter to diffuse into the colony for lysis employing strong base, followed by proteolysis with an appropriate protease and heating at an elevated temperature to fix the DNA.

An alternative technique may be employed using a gel for separation of the nucleotides by electrophoretic mobility. For RNA, the RNA is normally pretreated to remove interfering reagents. The RNA or DNA contained in the gel is then transferred to diazo-substituted paper. See Wahl et al. Proc. Natl. Acad. Sci. USA 76, 3683–3687 (1979).

Hybridization will be carried out under conditions which favor hybrid DNA complexing between RNA and DNA. Various hybridization buffer solutions may be employed as described in Wahl et al, supra; Stuart and Porter, supra. Normally, solutions of saline sodium citrate containing from about 30 to 60% formamide find use. Other additives may include sodium dodecylsulfate, ethylene diamine tetraacetic acid, ficoll (about 300–500 kdaltons), polyvinyl pyrrolidone (about 250–500 kdaltons), serum albumin, dextran sulfate (about 10,000 to 1,000,000 kdaltons), glycine (about 0.5–2% wt/vol), and about 0.5–5mg/ml of sonicated denatured DNA e.g. calf thymus or salmon sperm.

The temperature for the hybridization will generally vary from about room temperature to up to about 70° C., more usually from about 30° to 50° C.

The hybridization can be terminated by cooling, followed by washing or by washing at a temperature at a range of about 20° to 75° C. with an appropriate buffered solution, such as phosphate buffered saline or saline sodium citrate, containing minor amounts of various other additives such as sodium dodesyl sulfate, and the like.

The identification of the presence of the hybrids may now be achieved by employing monoclonal antibodies specific for the hybrid complex. Detection can be achieved by labeling either the monoclonal antibody specific for the hybrid DNA-RNA complex, hereinafter referred to as "anticomplex" or by employing labeled antibodies which bind to the anticomplex. For example, where the monoclonal antibody is derived from a mouse, antibodies to mouse antibodies e.g. rabbit anti(-mouse IgG), could be labeled so as to bind to any anticomplex bound to the complex bound to the solid support.

A wide variety of labels have been used in other environments which would be applicable here. One of the more common labels is radionuclides, which can be used with autoradiography to visualize the areas of binding. Another label is a fluorescer e.g. fluorescein, merocyanine, rhodamine, etc., which by irradiation with light of excitation, the presence of fluorescence can be monitored. Alternatively, an enzyme can be used which results in a product which can be detected and localized in the area of the enzyme. A large number of dyes or metals capable of reduction can be employed to provide detection. Common enzymes include horseradish peroxidase, glucose oxidase, $\beta$-galactosidase, or the like. The particular label or manner in which the detectable signal is observed is not critical to this invention. Evidently, by employing antibodies to the anticomplex, the number of labels associated with a particular binding of the anticomplex to the complex can be greatly amplified.

The following examples are offered by way illustration and not be way of limitation.

EXPERIMENTAL

Chromosomal Preparations

Salivary glands from larvae were excised in Grace's insect medium (GIBCO), fixed for 8-10 min. in methanol/acetic acid, 3:1 (vol/vol), placed on acid washed slides with one drop of 45% acetic acid, and squashed under siliconized coverslips. The preparations were held at $-20°$ C. for at least 30 min and then immersed in liquid nitrogen. After 1 min. the slides were withdrawn and the coverslips were removed by inserting a no. 10 surgical blade between the slide and the coverslip. The slides were immediately immersed in 95% ethanol. The slides remained in ethanol for at least 4 hr. prior to the in situ hybridization. Preparations may be stored in ethanol for up to 2 weeks without deterioration or structure of hybridization results.

RNA Probe

RNA was isolated from larvae quick-frozen in liquid nitrogen and stored at −70° C. for up to 2 weeks. The isolation method of Kirby ((1968) in Methods Enzymol. 12, 94–95) was used with the following modifications, sodium triisopropylnaphthalenesulfonate was substituted for sodium p-toluenesulfonate; the phenol/cresol extraction was repeated twice; and 3M NaCl was substituted for 3M sodium acetate to remove glycogen and tRNA. The high molecular weight RNA salt precipitate was resuspended and reprecipitated with 3M NaCl a total of three times. The final precipitate was resuspended and made 0.12M in NaCl, 0.01M in Tris.HCl at pH 7.6, 1 mM in EDTA, and 0.02% in sodium dodecylsulfate at an RNA concentration of 2 mg/ml and applied to an oligo(dT)-cellulose column to remove polyadenylated RNA species (Mezl and Hunt (1978) Biochem. J. 141, 617–625). RNA not adsorbed to the column was collected and precipitated with 2.5 vol of ethanol at −20° C. overnight. The precipitate was collected by centrifugation and resuspended at a concentration of 800 µg/ml in 0.01M Tris.HCl, pH7.4/1 mM EDTA/0.1M NaCl. At this point the RNA sample was further purified by either (a) sucrose gradient fractionation or (b) preparative electrophoresis as follows.

(a) A 500 µl sample of RNA was heated to 38° C. for 5 min. and applied directly to a 17 ml linear sucrose gradient (5–20%) made in the same buffer. Heating to 65° C. was avoided because this treatment results in the denaturation of the 28S rRNA species found in insects and the denatured RNA comigrates with the 18S species during centrifugation. The gradient was centrifuged in a Beckman instrument using an SW27.1 rotor at 25,000 rpm for 21.5 hr at 4° C. Fractions were collected and those containing 28S RNA were pooled, precipitated, and resuspended in hybridization solution (1:1 mixture of formamide and 0.6M NaCl/0.06M Na citrate, pH7).

(b) RNA (230 µg) was applied in 2.5 ml of sample buffer to a 6M urea/1% agarose gel (53×120 mm) formulated by the method of Long and David (1980) Cell 18, 1185–1196. The gel was run for 8 hr at 95 V(100 mA) and then stained for 15 min. with ethidium bromide. The portion of gel containing the large fragment of the denatured 28S rRNA was placed in a dialysis bag with 3 ml of gel buffer and electroeluted from the agarose for 3 hr. The eluted 28S fragment was precipitated with ethanol and resuspended in hybridization solution.

RNA purified by either method gave similar hybridization results.

In Situ Hybridization

Hybrids were prepared as reported by Stuart and Porter, supra. Estimates of hybridization rates were obtained by incubating preparations (sealed with rubber cement) at 70° C. for 1 hr and then immediately shifting the preparations to 40° C. by immersion in a thermostatted water bath. $C_r t$ values were calculated as initial concentration of the RNA probe in mol per liter multiplied by time(sec) of incubation at 40° C. The hybridization was terminated by immersion in an ice-water bath.

Antibody Production

Rabbit antibody to poly(rA)·poly(dT) hybrids complexed to methylated bovine serum albumin was prepared by the method of Stollar, (1970) Science 169, 609–611. Mouse monoclonal hybrid cell cultures to the same antigen were prepared by the method of Oi and Herzenberg, supra. Immunized spleen cells were fused with P3-NS-1 BALB/c myeloma cells (originally derived from the BALB/c-MOPC-21 cell line) provided by Douglas Vann. Positive fusion cultures were cloned by the limiting dilution method and a number of hybridomas were obtained. One positive clone (FS.B12-G10) was chosen for use in this study.

Identification of Hybrids

Regions of in situ hybridization were detected by secondary immunofluorescence as reported by Stuart and Porter, supra. Goat anti-rabbit and goat anti-mouse Ig antisera conjugated with fluorescein isothiocyanate were purchased from Antibodies, Inc. Preparations were examined under a Zeiss dark-field transmitted fluorescence system (quartz/halogen source, KP 500 excitation filter (Zeiss), and 530nm barrier filter). Photomicrographs were taken with Tri-X Pan film (Kodak ASA 400).

The rabbit antiserum and mouse hybridoma antibodies were tested for specificity. When no RNA probe was present during the hybridization and the preparation was redigested with RNase A, no secondary fluorescent bands were observed. When the RNA normally present in the polytene preparation was not predigested with RNase A, multiple fluorescent bands were observed after hybridization. This evidences that the antibodies were not reactive with chromosomal DNA but were able to bind to RNA-DNA duplexes. Absorption of antibody reagents with single stranded poly(rA)-methylated albumin complexes with poly(dT)-methylated albumin complexes did not reduce immunofluorescent visualization of in situ RNA-DNA hybrids. Absorption of antibody reagents with poly(rA)-poly(dT) duplexes complexed to methylated albumin removed all activity responsible for the secondary immunofluorescent bands. Therefore, the antibodies recognized RNA-DNA hybrids, but not other forms of RNA or DNA.

Several hundred preparations from both *D. silvesteris* and *D. heteroneura* were examined for localization of the 18/28S rRNA locus. After the fluorescent regions were hybridized, a phase condenser was inserted into the system and phase-contrast photomicrographs were taken. The coverslip was then removed and the preparation stained with acetoorcein. A fresh coverslip was then added to the stained preparation, producing a conventionally banded aspect. This procedure allowed the placement of the in situ hybrid band unequivocally at the chromosome three locus.

In mature larval cells the nucleolus showed little or no fluorescence. In cells obtained from younger larvae fluorescent staining of the nucleolus was very strong. This indicates that either the DNA sequences for 18/28S rRNA are present in the nucleolus during early larval development but are not available for hybridization at the third-instant larval stage immediately prior to pupation or the subject method is not capable of visualizing the sequences in the enlarged nucleolus. Hybridization of 28S rRNA to the young larval cells identified with mouse monoclonal antibodies was evidenced by secondary immunofluorescence with counter-staining by fluorescence microscopy with 1500 magnification. Hybridization to a single band in the genome is visible.

Hybridization was performed at $C_rt$ values ranging from $1 \times 10^{-4}$ to $4 \times 10^1$ to determine if the rate of hybridization was consistent with that expected for 18/28S rRNA. Results have been reported by Szabo et al (1977) J. Mol. Biol. 115, 539–563, reporting $C_rt$ curves and rate constants for both 5S and 18/28S rRNA of D. melanogaster hybridized in situ under conditions similar to those used here. Faint fluorescence of both the nucleolus and the chromosome 3 band at a $C_rt$ value of $\times 10^{-2}$ was observed.

The subject invention provides for an accurate and simple technique for detecting the presence of a particular nucleic acid sequence by hybridization in situ. The use of monoclonal antibodies substantially precludes significant binding to single stranded nucleic acids for double stranded DNA or RNA. Thus, by employing a probe having a complementary sequence to the alternative type of nucleic acid e.g. DNA with RNA, the presence of the sequence either by itself or as part of a much larger sequence may be readily detected. Furthermore, by appropriate use of hybridization conditions and rates, one can readily determine the proportionate homology of the sample to the probe. The subject method and compositions therefore provides great flexibility in being able to determine the presence of a particular nucleic acid sequence, having application for the detection of genes, structural, regulatory or expressing RNA, the presence of mutations, and the like.

The hybridomas designated in this application as G10 H4, G11 K3, and A6 P3 were deposited with the American Type Culture Collection, Rockville, Md., where they have been given ATCC numbers HB 8076, HB 8077 and HB 8078.

Although the foregoing invention has been described in some detail by way of illustration and example for purposes of clarity of understanding, it will be obvious that certain changes and modifications may be practiced within the scope of the appended claims.

What is claimed is:

1. A hybridoma cell line which produces an IgM or IgG mouse monoclonal antibody which specifically binds to DNA-RNA hybrid complexes but which does not bind to isolated RNA or DNA.

2. The hybridoma of claim 1, wherein said antibody is IgM.

3. The hybridoma of claim 1, wherein said antibody is IgG.

* * * * *